United States Patent
Paterson et al.

(10) Patent No.: US 11,364,488 B2
(45) Date of Patent: Jun. 21, 2022

(54) SUPPORTED COBALT-CONTAINING FISCHER-TROPSCH CATALYST, PROCESS FOR PREPARING THE SAME AND USES THEREOF

(71) Applicant: BP P.L.C., London (GB)

(72) Inventors: Alexander James Paterson, Hull (GB); Zhaorong Zhang, Naperville, IL (US)

(73) Assignee: BP P.L.C., London (GB)

( * ) Notice: Subject to any disclaimer, the term of this patent is extended or adjusted under 35 U.S.C. 154(b) by 0 days.

(21) Appl. No.: 17/040,213

(22) PCT Filed: Mar. 21, 2019

(86) PCT No.: PCT/EP2019/057061
§ 371 (c)(1),
(2) Date: Sep. 22, 2020

(87) PCT Pub. No.: WO2019/180125
PCT Pub. Date: Sep. 26, 2019

(65) Prior Publication Data
US 2021/0008527 A1    Jan. 14, 2021

Related U.S. Application Data

(60) Provisional application No. 62/646,566, filed on Mar. 22, 2018.

(51) Int. Cl.
*B01J 23/75* (2006.01)
*B01J 21/06* (2006.01)
(Continued)

(52) U.S. Cl.
CPC .............. *B01J 23/75* (2013.01); *B01J 21/063* (2013.01); *B01J 35/026* (2013.01);
(Continued)

(58) Field of Classification Search
CPC .... B01J 23/75; B01J 35/1061; B01J 37/0201; B01J 37/0236; B01J 37/088; B01J 37/16; C10G 2/333; C10G 51/00
See application file for complete search history.

(56) References Cited

FOREIGN PATENT DOCUMENTS

| RU | 2182137 C1 | 5/2002 |
| WO | WO 1999/034917 A1 | 7/1999 |

(Continued)

OTHER PUBLICATIONS

Angelov, S. et al. "Cobalt hydroxide nitrate hydrate, Co(OH)(NO3).cntdot.H20: a novel double-chain compound with competing interaction." Inorganic Chemistry, 1992, 31(8), p. 1514-1517.
(Continued)

*Primary Examiner* — Jafar F Parsa
(74) *Attorney, Agent, or Firm* — McDonnell Boehnen Hulbert & Berghoff LLP

(57) ABSTRACT

The present invention relates to a process for preparing a cobalt-containing Fischer-Tropsch synthesis catalyst with good physical properties and high cobalt loading. In one aspect, the present invention provides a process for preparing a supported cobalt-containing Fischer-Tropsch synthesis catalyst, said process comprising the steps of: (a) impregnating a support material with cobalt haydroxide nitrate, or a hydrate thereof, of formula (I) below to form an impregnated support material, $[Co(OH)_x(NO_3)_{(2-x)} \cdot yH_2O]$ (I) where: $0 < x < 2$, $0 \leq y \leq 6$ (b) drying and calcining the impregnated support material.

28 Claims, 2 Drawing Sheets

(cont.)

(51) Int. Cl.
*B01J 35/02* (2006.01)
*B01J 35/10* (2006.01)
*B01J 37/00* (2006.01)
*B01J 37/02* (2006.01)
*B01J 37/08* (2006.01)
*B01J 37/16* (2006.01)
*C07C 1/04* (2006.01)
*C10G 2/00* (2006.01)

(52) U.S. Cl.
CPC ....... *B01J 35/1057* (2013.01); *B01J 35/1061* (2013.01); *B01J 37/0009* (2013.01); *B01J 37/0201* (2013.01); *B01J 37/0236* (2013.01); *B01J 37/088* (2013.01); *B01J 37/16* (2013.01); *C07C 1/0435* (2013.01); *C10G 2/332* (2013.01); *C07C 2521/06* (2013.01); *C07C 2523/75* (2013.01)

(56) References Cited

FOREIGN PATENT DOCUMENTS

| WO | WO 2010/097754 A2 | 9/2010 |
| WO | WO 2011/062773 A2 | 5/2011 |
| WO | WO 2012/146950 A1 | 11/2012 |
| WO | WO 2016/097402 A1 | 6/2016 |

OTHER PUBLICATIONS

Petrov, K. et al., "Preparation and X-ray diffraction characterization of two modifications of the cobalt hydroxide nitrate Co(OH)NO3 • H2O." J. Solid State Chem., 1992, 101, p. 145-153.

Markov, L. et al., "On the thermal decomposition of some cobalt hydroxide nitrates." Thermochim Acta, 1986, 106, p. 283-292.

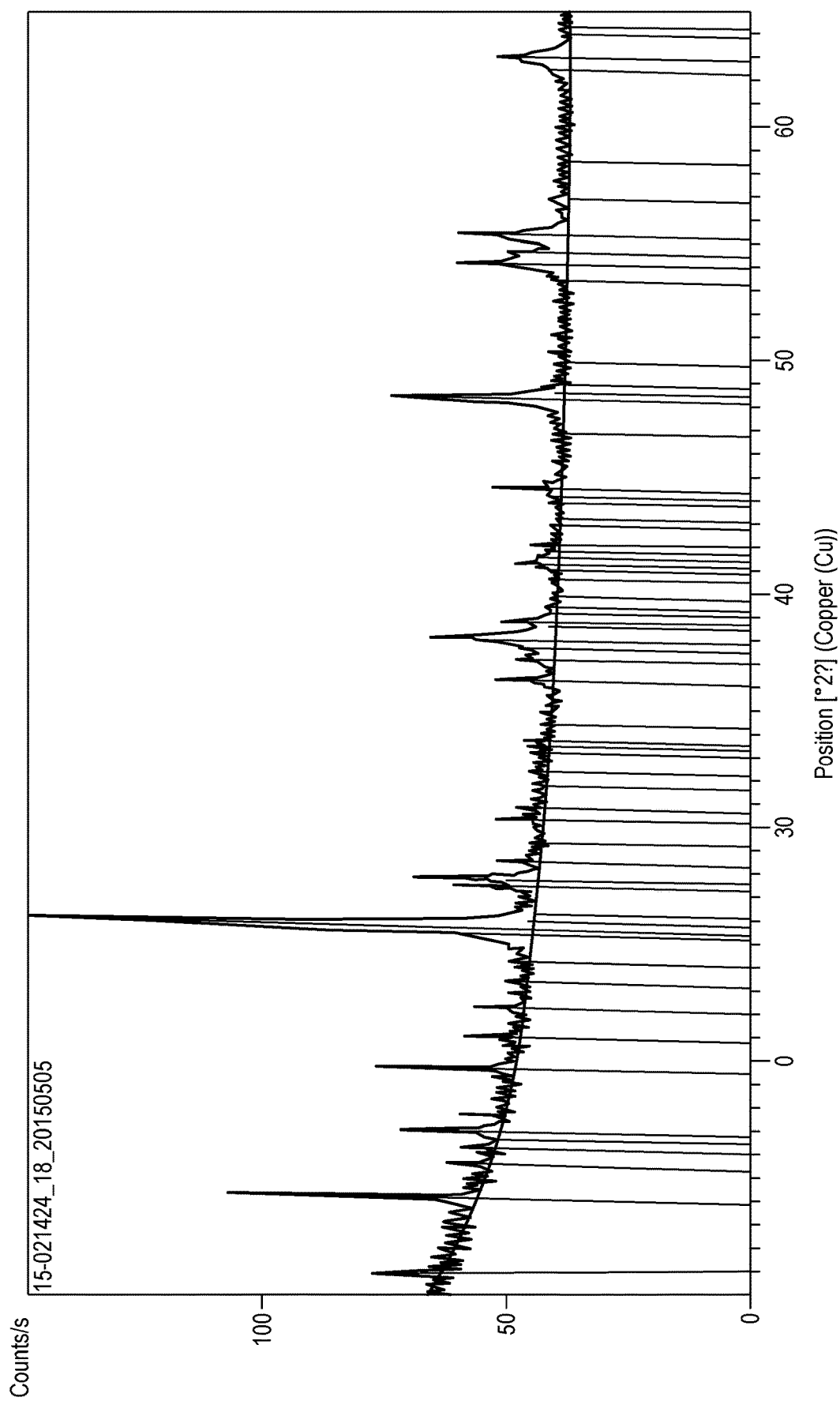

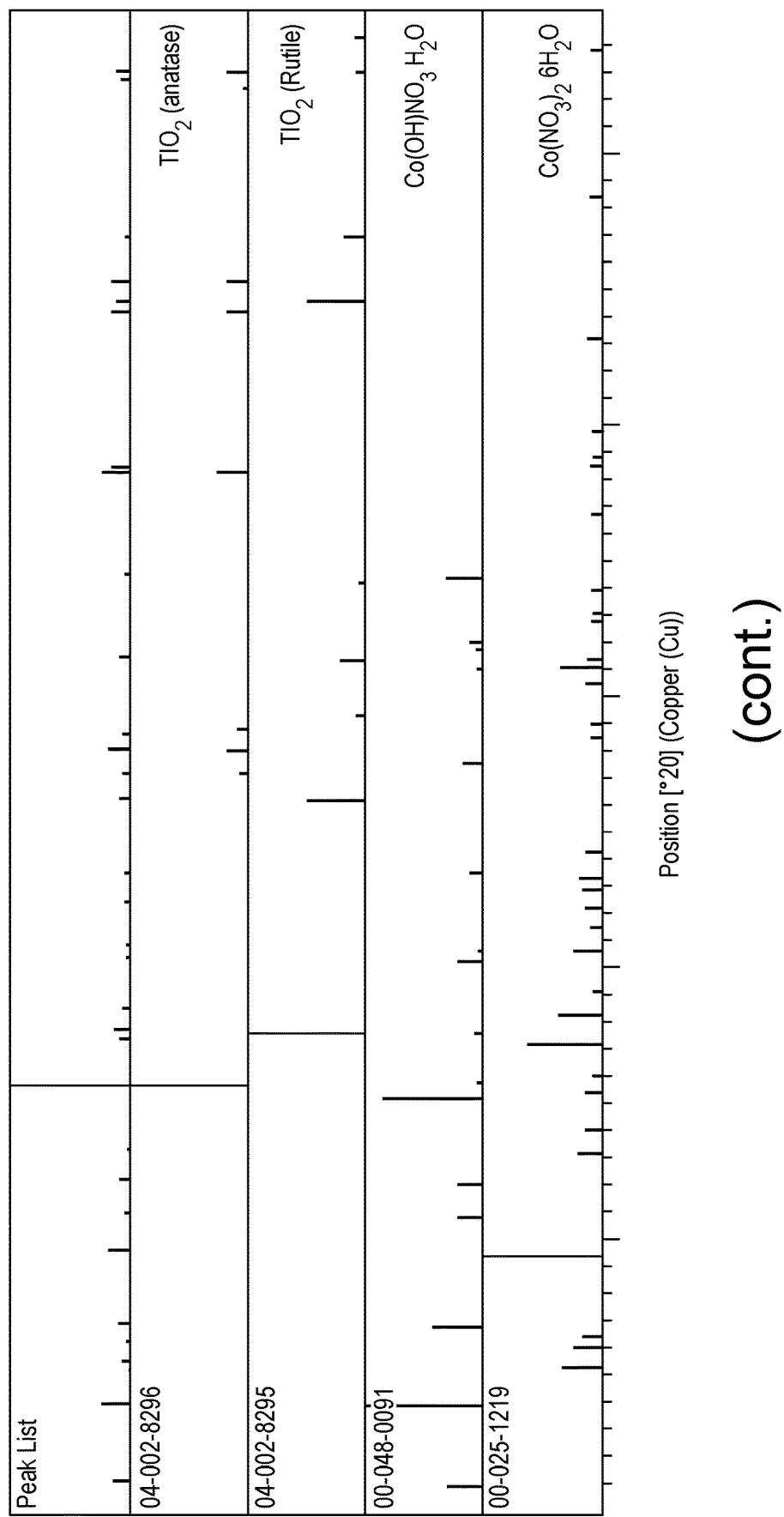

SUPPORTED COBALT-CONTAINING FISCHER-TROPSCH CATALYST, PROCESS FOR PREPARING THE SAME AND USES THEREOF

The present application is a U.S. National Stage filing under 35 U.S.C. § 371 of International Patent Application no. PCT/EP2019/057061, filed Mar. 21, 2019, which claims the benefit of priority of U.S. Provisional application No. 62/646566, filed on Mar. 22, 2018, both of which are incorporated herein by reference in their entirety.

The present invention relates to a process for preparing a supported cobalt-containing Fischer-Tropsch synthesis catalyst and use of the same in a Fischer-Tropsch reaction. In particular, the supported cobalt-containing Fischer-Tropsch synthesis catalyst is prepared by utilising a cobalt source in the form of a cobalt hydroxide nitrate compound, or a hydrate thereof. The invention also provides uses of the supported cobalt-containing Fischer-Tropsch synthesis catalyst prepared by the process as well as a process for preparing the cobalt hydroxide nitrate compound, or a hydrate thereof, which is employed as the cobalt source.

The conversion of synthesis gas into hydrocarbons by the Fischer-Tropsch process has been known for many years. The growing importance of alternative energy sources has seen renewed interest in the Fischer-Tropsch process as one of the more attractive direct and environmentally acceptable routes to high quality transportation fuels.

Many metals, for example cobalt, nickel, iron, molybdenum, tungsten, thorium, ruthenium, rhenium and platinum are known to be catalytically active, either alone or in combination, in the conversion of synthesis gas into hydrocarbons and oxygenated derivatives thereof. Of the aforesaid metals, cobalt, nickel and iron have been studied most extensively. Generally, the metals are used in combination with a support material, of which the most common are alumina, silica and carbon.

In the preparation of cobalt-containing Fischer-Tropsch catalysts, a solid support is typically impregnated with a cobalt-containing compound, which may for instance be an organometallic or inorganic compound (e.g. $Co(OH)_2$ and $Co(NO_3)_2 \cdot 6H_2O$), by contacting with a solution of the compound. The particular form of cobalt-containing compound is typically selected for its ability to form a cobalt oxide (for instance, $CoO$, $Co_2O_3$ or $Co_3O_4$) following a subsequent calcination/oxidation step.

Following generation of the supported cobalt oxide, a reduction step is necessary in order to form the pure cobalt metal as the active catalytic species. Thus, the reduction step is also commonly referred to as an activation step. Various different methods of either activating a fresh Fischer-Tropsch catalyst or regenerating a used Fischer-Tropsch catalyst are known.

A principal focus in adapting Fischer-Tropsch synthesis catalysts is for improving activity and selectivity for $C_{5+}$ hydrocarbons, in particular paraffinic hydrocarbons. It is generally understood that selectivity for $C_{5+}$ hydrocarbons in the Fischer-Tropsch synthesis reaction is increased by operating at lower temperatures. By providing a catalyst of higher activity, it may be possible to achieve the same level of synthesis gas conversion at lower temperatures whilst benefitting from improved $C_{5+}$ hydrocarbon selectivity. As such, a catalyst of higher activity also represents a means for modifying the selectivity of the Fischer-Tropsch synthesis by allowing a reduction in operating temperature. A further focus in adapting Fischer-Tropsch synthesis catalysts is for increasing conversion of synthesis gas or other mixtures of hydrogen and carbon monoxide gases into hydrocarbons.

Previous research has revealed that content of cobalt in the catalysts is a decisive factor for the on-stream performance of Fischer-Tropsch catalysts. A loading of up to approximately 10 wt. % of cobalt on elemental basis has been readily achievable per impregnation step with a fully dissolved solution of cobalt-containing compound, without compromising the physical properties of the supported Fischer-Tropsch synthesis catalyst. Impregnating a support powder or granulate with such a solution also ensures that a mixture is obtained which is suitable for extrusion. It has been observed that larger volumes of solution corresponding to higher loadings of cobalt-containing compound can lead to problems with consistency which can preclude satisfactory shaping of the impregnated support material by extrusion.

The formation of cobalt-containing extrudates from commercially available preformed extrudates exhibits similar limitations on the concentration of cobalt that may be achieved on the supported catalyst in a single impregnation step. As described for instance in WO 2011/062773 and WO 99/34917, a single impregnation step with a solution of a cobalt-containing compound has historically been incapable or have struggled to achieve a cobalt metal loading of above 10 wt. %.

As such, multiple impregnations are typically required to afford extrudates with metal loadings which may only be marginally higher, yet for significant additional costs, as described, for instance, in WO 2016/097402.

Furthermore, using partially undissolved solid solutions, which require lower volumes of liquid, can negatively impact the distribution of cobalt-containing compound across the support and in some cases can lead to poor morphology and low bulk crush strength in an extrudate.

WO 99/34917 describes a process for forming an extrudate with appreciably higher cobalt metal loading of, for instance, 20 wt. %, through a single impregnation with a partially undissolved solution (a 'solid solution') of a cobalt-containing compound. Such a solid solution may be formed by precipitation of the cobalt compound following the addition of a base to a solution of soluble cobalt-containing compound. Although the method reported in WO 99/34917 is capable of forming extrudates with higher cobalt metal loadings, and thus higher catalyst activities, than was previously possible in a single impregnation step, the extrudates obtained by this method suffer from low bulk crush strength and poor morphology.

Thus, in obtaining higher cobalt metal loading, the advantages associated with using an extrudate are in effect negated. Furthermore, the use of a solid solution for impregnating the support material particulate has previously been observed to result in a poor dispersion of cobalt-containing compound over the surface and in the pores of the support material which can negatively impact upon catalyst performance and lifetime.

It is known that cobalt hydroxide is less soluble than cobalt nitrate and hydrates thereof and therefore higher cobalt concentrations can be attained per unit volume of solvent where cobalt nitrate and hydrates thereof are employed. However, cobalt nitrate is hygroscopic and therefore, following deposition on a support material, a degree of metal dilution can occur at the surface as a result of moisture uptake. Upon calcination, there is substantial loss of volume due to the conversion of the cobalt nitrate to cobalt oxide and the loss of the water of crystallisation, impacting on the density of the cobalt oxide crystallites per unit area at the surface of the support. This is thought to contribute to the lower maximum cobalt loadings that have been achieved historically by means of a single impregnation step where, for instance, cobalt nitrate hexahydrate is employed as the cobalt source.

There remains a need for an improved process for producing a Fischer-Tropsch synthesis catalyst with high cobalt loading in a single impregnation step, so that the reduced catalyst benefits from higher activity whilst retaining good physical properties, including bulk crush strength and morphology. Moreover, there remains a need for an alternative process for preparing a Fischer-Tropsch synthesis catalyst which may be used to improve conversion and selectivity for $C_{5+}$ hydrocarbons in Fischer-Tropsch reactions, which hydrocarbons are of most value for preparing fuel compositions.

It has now surprisingly been found that a supported cobalt-containing Fischer-Tropsch catalyst having high cobalt metal loading, for instance, in excess of 15 wt. %, may be prepared in a single impregnation step using a cobalt hydroxide nitrate compound, or a hydrate thereof, as the cobalt source. This compound has a greater proportion of cobalt (percentage by weight), and is less hygroscopic, when compared to cobalt nitrate hexahydrate which historically has been the cobalt source of choice in the preparation of cobalt-containing Fischer-Tropsch catalysts. The Fischer-Tropsch catalyst obtainable from using the cobalt hydroxide nitrate compound as the source of cobalt has been found to have high conversion and good selectivity for $C_{5+}$ hydrocarbons.

In a first aspect, the present invention provides a process for preparing a supported cobalt containing Fischer-Tropsch synthesis catalyst, said process comprising the steps of:
(a) impregnating a support material with cobalt hydroxide nitrate, or a hydrate thereof, of formula (I) below to form an impregnated support material, $$[Co(OH)_x(NO_3)_{(2-x)}.yH_2O] \quad (I)$$

where: $0<x<2$, and
$0 \leq y \leq 6$;
(b) drying and calcining the impregnated support material.

In a second aspect, the present invention provides a process for preparing a supported cobalt containing Fischer-Tropsch synthesis catalyst, said process comprising the steps of:
(i) impregnating a support material with cobalt hydroxide nitrate, or a hydrate thereof, of formula (I) below to form an impregnated support material, $$[Co(OH)_x(NO_3)_{(2-x)}.yH_2O] \quad (I)$$

where: $0<x<2$, and
$0 \leq y \leq 6$;
(ii) forming shaped particles from the impregnated support material; and
(iii) drying and calcining the shaped particles.

In other aspects, the invention provides a Fischer-Tropsch synthesis catalyst obtained or obtainable by the process defined above as well as a process for converting a feed comprising a mixture of hydrogen and carbon monoxide gases into hydrocarbons which employs the cobalt-containing Fischer-Tropsch synthesis catalyst.

Also provided are methods and uses of a cobalt-containing Fischer-Tropsch synthesis catalyst as defined above for increasing the selectivity of a Fischer-Tropsch process for the production of $C_{5+}$ hydrocarbons and/or increasing conversion in a Fischer-Tropsch process.

Also provided is the use of the cobalt hydroxide nitrate of formula (I) as defined above for increasing the elemental cobalt metal loading on supported cobalt-containing Fischer-Tropsch synthesis catalyst which is obtainable in a single impregnation step.

In yet a further aspect, the invention also provides a process for preparing cobalt hydroxide nitrate, or a hydrate thereof, of formula (I):

$$[Co(OH)_x(NO_3)_{(2-x)}.yH_2O] \quad (I)$$

where: $0<x<2$; and
$0 \leq y \leq 6$,
said process comprising the step of reacting cobalt hydroxide with cobalt nitrate.

In the first aspect, the present invention provides a process for preparing a supported cobalt containing Fischer-Tropsch synthesis catalyst, said process comprising the steps of: (a) impregnating a support material with cobalt hydroxide nitrate to form an impregnated support material; and, (b) drying and calcining the impregnated support material.

In the second aspect, the present invention provides a process for preparing a supported cobalt-containing Fischer-Tropsch synthesis catalyst, said process comprising the steps of: (i) impregnating a support material with cobalt hydroxide nitrate to faun an impregnated support material; (ii) forming shaped particles from the impregnated support material; and (iii) drying and calcining the shaped particles.

Reference herein to cobalt hydroxide nitrate, unless otherwise specified, refers to a cobalt hydroxide nitrate compound, or a hydrate thereof, of formula (I):

$$[Co(OH)_x(NO_3)_{(2-x)}.yH_2O] \quad (I)$$

where: $0<x<2$
$0 \leq y \leq 6$

In formula (I), x and y are not required to be integers, and may often be numbers which are not integers.

In formula (I), x is greater than 0 and is less than 2. In some or all embodiments, x is at most 1.5. In some or all embodiments, x is at most 1. In some or all embodiments, x is at least 0.1. In some or all embodiments, x is at least 0.2.

In formula (I), y is equal to or greater than 0, and is equal to or less than 6.

In some or all embodiments, formula (I) may be written as formula (I'):

$$[Co_p(OH)_q(NO_3)_r.zH_2O] \quad (I')$$

where: p, x and y are integers greater than zero
$p=(q+r)/2$; and
$0 \leq z \leq 6p$;

In some embodiments, p is 1, 2, 3, 4, 5, 6, 7, 8, 9 or 10.
In preferred embodiments, p is an integer greater than 1, for example from 2 to 10 or from 2 to 8.
In some embodiments, q is 1, 2, 3, 4, 5, 6, 7, 8, 9, 10, 11, 12, 13, 14, 15, 16, 17, 18, 19 or 20.
In preferred embodiments, q is an integer greater than 1, for example from 2 to 20, from 2 to 16, or from 2 to 12.
In some embodiments, r is 1, 2, 3, 4 or 5.
In other embodiments, r is 1, 2 or 3 or r is 1 or 2.
In some embodiments, z is from 0.1 to 10, from 0.2 to 8, or from 0.25 to 5.

In some or all embodiments of the present invention, the cobalt hydroxide nitrate is selected from $Co(OH)(NO_3).H_2O$, $Co_2(OH)_3(NO_3).0.25H_2O$ and $Co_7(OH)_{12}(NO_3)_2.5H_2O$.

Without wishing to be bound by any particular theory, it is believed that the cobalt hydroxide nitrate described hereinabove may accommodate a higher cobalt concentration in the impregnation solution, which in turn leads to a greater concentration of cobalt that may be deposited on the support material during impregnation. This is believed to derive from both good solubility properties of the cobalt hydroxide nitrate in the impregnating solution in combination with a higher weight percentage of cobalt in the compound in comparison to conventional cobalt sources such as cobalt nitrate hexahydrate. Moreover, lower hydroscopicity associated with cobalt hydroxide nitrate of formula (I) in comparison, for instance, to cobalt nitrate hexahydrate means that the compound of formula (I) may be more densely loaded in the volume of the support material following impregnation. This allows for increased elemental cobalt loading on the supported catalyst to be obtained in a single impregnation step.

Reference herein to "impregnation", "impregnating", "impregnated" or related terms is intended to refer to contacting a support material, such as preformed shaped particle/extrudate or a support powder or granulate, with a solution of cobalt hydroxide nitrate before drying in order to achieve precipitation of the cobalt hydroxide nitrate.

The impregnation solution may or may not be fully dissolved, depending upon the concentration of the cobalt hydroxide nitrate in the solvent. However, it has been found that it is not necessary for the impregnation to be performed with a fully dissolved solution of cobalt hydroxide nitrate to ensure good dispersion of cobalt hydroxide nitrate on the support material, the benefits of the present invention can also be realised in the case where a solution of partially undissolved cobalt hydroxide nitrate is used.

The support material used with the present invention is not particularly limited and may be selected from any suitable refractory metal oxide or silicates known in the art, or combinations thereof. Preferably, the support material is selected from the group consisting of silica, alumina, silica-alumina, ceria, gallia, zirconia, titania, magnesia, zinc oxide, and mixtures thereof. More preferably, the support material is selected from titania and zinc oxide. Most preferably, the support material is selected from titania or mixtures containing titania. Titania may be selected from titanium dioxide anatase, titanium dioxide rutile, titanium dioxide brookite and combinations thereof. An example of a preferred titania support material particulate is titania powder, e.g. P25 Degussa.

Reference herein to a "preformed" support or "shaped particle" is intended to mean a shaped solid support (for instance, by extrusion) suitable for impregnation, for instance by incipient wetness. The preformed support may, for instance, have a geometrically symmetrical shape, examples of which include a cylinder, sphere, cylindrical dilobe, cyclindrical trilobe, cylindrical quadrolobe or a hollow cyclinder. Preferably, the preformed support has not undergone any impregnation steps to introduce cobalt-containing compounds, or any other materials thereto, and impregnation step (a) is the only step in which a cobalt-containing compound is introduced to the support material prior to calcination in step (b). However, preformed supports may be used which have undergone pre-treatments, for instance, the introduction of promoters, dispersion aids, strength aids, binders or other additives. Pre-treatments of the preformed support may also include physical pre-treatments, such as granulation prior to formation of the shaped solid support.

Reference herein to a powder or granulate of a support material is understood to refer to free flowing particles of a support material or particles of support material that have undergone granulation to be a particular shape (e.g. spherical) and size range. In the context of the present invention, the powder or granulate is in a form which is suitable for impregnation by means of a solution of cobalt hydroxide nitrate and subsequent extrusion. Preferably, the powder or granulate of a support material, when used as a starting material in the process of the invention, has not undergone any impregnation steps to introduce cobalt-containing compound, or any other materials thereto. Alternatively or in addition, impregnation step (a) in the first aspect of the invention, or step (i) in the second aspect of the invention, is preferably the only step in which a cobalt-containing compound is introduced to the support material prior to calcination in step (b) in the first aspect of the invention, or step (iii) in the second aspect of the invention. However, powders or granulates of a support material may be used which have undergone pre-treatments so as to, for instance, introduce promoters, dispersion aids, strength aids, binders or other additives. Pre-treatments of the powders or granulates of a support material may also include physical pre-treatments, such as sieving.

Preferred support materials are substantially free of extraneous metals or elements which might adversely affect the catalytic activity of the system. Thus, preferred support materials are at least 95% w/w pure, more preferably at least 99% w/w pure. Impurities preferably amount to less than 1% w/w, more preferably less than 0.60% w/w and most preferably less than 0.30% w/w. The pore volume of the support is preferably more than 0.20 ml/g and preferably more than 0.5 ml/g. The average pore radius (prior to impregnation with cobalt hydroxide nitrate) of the support material is 10 to 500 Å, preferably 15 to 100 Å, more preferably 20 to 80 Å and most preferably 25 to 40 Å. The BET surface area is preferably from 2 to 1000 $m^2$ g, preferably from 10 to 600 $m^2/g$, more preferably from 15 to 100 $m^2/g$, and most preferably 30 to 60 $m^2/g$.

The BET surface area, pore volume, pore size distribution and average pore radius may be determined from the nitrogen adsorption isotherm determined at 77K using a Micromeritics TRISTAR 3000 static volumetric adsorption analyser. A procedure which may be used is an application of British Standard methods BS4359:Part 1:1984 'Recommendations for gas adsorption (BET) methods' and BS7591: Part 2:1992, 'Porosity and pore size distribution of materials'—Method of evaluation by gas adsorption. The resulting data may be reduced using the BET method (over the pressure range 0.05-0.20 P/Po) and the Barrett, Joyner & Halenda (BJH) method (for pore diameters of 20-1000 Å) to yield the surface area and pore size distribution respectively.

Suitable references for the above data reduction methods are Brunauer, S, Emmett, P H, & Teller, E, J. Amer. Chem. Soc. 60, 309, (1938) and Barrett, E P, Joyner, LG & Halenda P P, J. Am Chem. Soc., 1951 73 373-380.

In preferred embodiments, where a powder of support material is employed as the starting material, the powder has a median particle size diameter (d50) of the less than 50 μm, preferably less than 25 μm. Particle size diameter (d50) may suitably be determined by means of a particle size analyser (e.g. Microtrac 53500 Particle size analyser).

In preferred embodiments, where the support material is in the form of a granulate, the median particle size diameter (d50) is in the range 300 to 600 vim.

When a support material is in the form of a powder or granulate, the impregnation step may form an impregnated support powder or granulate. In the second aspect of the invention, such an impregnated support powder or granulate may then be formed into a shaped particle in step (ii), prior to drying and calcining in step (iii). In an embodiment of the second aspect of the present invention, impregnated support powder or granulate is extruded to form an extrudate prior to drying and calcining in step (iii).

Alternatively, when a support material is in the form of a powder or granulate, the impregnation step may form an impregnated support powder or granulate in step (a) according to the first aspect of the invention, this impregnated support powder or granulate may undergo drying and calcining in step (b) to form a calcined powder or granulate, following which the calcined powder or granulate may then be formed into a shaped particle, for example by extrusion to form an extrudate.

In embodiments wherein the support material is in the form of a shaped particle, for example an extrudate, impregnation step (a) may form an impregnated shaped particle, for example an impregnated extrudate, prior to drying and calcining in step (b) in accordance with the first aspect of the invention.

Impregnation of the support material with the cobalt hydroxide nitrate compound in accordance with the present invention may be achieved by any suitable method of which the skilled person is aware, for instance by vacuum impregnation, incipient wetness or immersion in excess liquid. The solvent of the impregnating solution may be either an aqueous solvent or a non-aqueous, organic solvent. Suitable non-aqueous organic solvents include, for example, alcohols (e.g. methanol, ethanol and/or propanol), ketones (e.g. acetone), liquid paraffinic hydrocarbons and ethers. Alternatively, aqueous organic solvents, for example an aqueous alcoholic solvent, may be employed. Preferably, the solvent of the impregnating solution is water and in some or all embodiments the support material is impregnated with an aqueous solution or suspension of cobalt hydroxide nitrate.

The concentration of the cobalt hydroxide nitrate in the impregnating solution is not particularly limited. When a powder or granulate of a support material is impregnated and immediately followed by an extrusion step, the amount of the impregnating solution is preferably suitable for forming an extrudable paste. In some or all embodiments, the concentration of the impregnating solution is sufficient to afford greater than or equal to 15 wt. % of cobalt loading, preferably from 15 wt. % to 20 wt. % of cobalt loading, on an elemental basis, in the supported synthesis catalyst based on the total weight of the supported synthesis catalyst. A suitable concentration of cobalt-containing compound is, for example, 0.1 to 15 moles/litre.

Impregnation of the support material in accordance with the present invention also involves sufficient drying of the impregnating solution in order to effect precipitation of the cobalt hydroxide nitrate on to the support material and preferably also to remove bound solvent of the impregnating solution (e.g. water). Drying therefore does not lead to decomposition of the cobalt hydroxide nitrate or otherwise lead to a change in oxidation state of the cobalt. As will be appreciated, in embodiments where an extrusion is performed, complete drying and removal of solvent (e.g. bound solvent) of the impregnating solution may occur after extrusion. Drying in accordance with the present invention is suitably conducted at temperatures from 50° C. to 150° C., preferably 75° C. to 125° C. Suitable drying times are from 5 minutes to 24 hours. Drying may suitably be conducted by any means known in the art, suitable examples include drying in a drying oven or in a box furnace, for example, under the flow of an inert gas at elevated temperature.

Where a preformed support or an extrudate is impregnated in accordance with the present invention, it will be appreciated that the support may be contacted with the impregnating solution by any suitable means including, for instance, vacuum impregnation, incipient wetness or immersion in excess liquid.

Where a powder or granulate of support material is impregnated, the powder or granulate may be admixed with the impregnating solution by any suitable means of which the skilled person is aware, such as by adding the powder or granulate to a container of the impregnating solution, or vice versa, and stirring the resulting solution. Where an extrusion step immediately follows impregnation of a powder or granulate, the mixture of powder or granulate and impregnating solution may be further processed if it is not already in a form which is suitable for extruding. For instance, the mixture may be mulled to reduce the presence of larger particles that may not be readily extruded, or the presence of which would otherwise compromise the physical properties of the resulting extrudate. Mulling typically involves forming a paste which is suitable for shaping by extrusion. Any suitable mulling or kneading apparatus of which the skilled person is aware may be used for mulling in the context of the present invention. For example, a pestle and mortar may suitably be used in some applications whilst a Vinci mixer or a Simpson muller may suitably be employed in others. Mulling is undertaken for a period sufficient to achieve the desired consistency, in some or all embodiments this may be for a period of from 3 to 90 minutes, such as for a period of 5 minutes to 30 minutes. Mulling may suitably be undertaken over a range of temperatures, including ambient temperatures. A preferred temperature range for mulling is from 15° C. to 50° C. Mulling may suitably be undertaken at ambient pressures. The solvent content of the mixture prior to extrusion may be adjusted if required, for example with the solvent used for impregnation, so as to attain an extrudable paste. As stated hereinbefore, it will be appreciated that complete removal of bound solvent from the impregnation solution may be conducted to effect complete precipitation after extrusion.

As part of an extrusion step, a shaped extrudate may be formed. The extrudate may, for instance, have a geometrically symmetrical shape, examples of which include a cylinder, sphere, cylindrical dilobe, cyclindrical trilobe, cylindrical quadrolobe or a hollow cyclinder.

In embodiments where a calcination step is performed on an impregnated powder or granulate, thereby completely removing solvent of the impregnation solution, the calcined powder or granulate may also be further processed in order to form a mixture which is suitable for forming shaped particles, such as by extrusion. For example, an extrudable paste may be formed by combining the calcined powder or granulate with a suitable solvent, for example a solvent used for impregnation, preferably an aqueous solvent, and mulled as described above.

In accordance with the process of the present invention, preparation of the supported Fischer-Tropsch synthesis catalyst involves a calcination step. Calcination, as discussed hereinbefore, is required for converting the cobalt hydroxide nitrate which has been impregnated on the support material into an oxide of cobalt. Thus, calcination leads to thermal decomposition of the cobalt hydroxide nitrate, and not merely removal of bound solvent of an impregnating solution, as in the case of drying in accordance with the present disclosure.

Calcination may be performed by any method known to those of skill in the art, for instance in a fluidized bed or rotary kiln at a temperature suitably in the range of from 150° C. to 700° C. In embodiments, calcining in step (b) of the first aspect of the invention, or step (iii) of the second aspect of the invention, is conducted at a temperature of at least 250° C., preferably from 275° C. to 500° C. Calcination may be conducted as part of an integrated process where calcination and reductive activation of the synthesis catalyst to yield the reduced synthesis catalyst are performed in the same reactor.

The process of the present invention has been found to be particularly suitable for increasing the loading of cobalt on a supported Fischer-Tropsch synthesis catalyst. The amount of cobalt, on an elemental basis, on the supported synthesis catalyst obtained in the impregnation step of the present invention is preferably greater than or equal to 10 wt. %, 11 wt. %, 12 wt. %, 13 wt. %, 14 wt. %, 15 wt. %, 16 wt. %, 17 wt. % or 18 wt. %, based on the total weight of the synthesis catalyst. In some or all embodiments of the present invention, the range of cobalt concentrations, on an elemental basis, for the synthesis catalyst obtained in accordance with the process of the present invention is from 15 to 20 wt. %, based on the total weight of the synthesis catalyst. As will be appreciated by the skilled person, the amount of cobalt, on an elemental basis, on the synthesis catalyst may be readily determined by x-ray fluorescence (XRF) techniques. Furthermore, as will be appreciated by the skilled person, identification of the cobalt-containing compound or other types of compound deposited on or comprising the support material may be performed by X-ray diffraction (XRD) techniques, in particular powder X-ray diffraction (PXRD) techniques.

The supported Fischer-Tropsch synthesis catalyst prepared in accordance with the process of the present invention may additionally comprise one or more promoters, dispersion aids, strength aids and/or binders. Promoters may be added to promote reduction of an oxide of cobalt to cobalt metal, preferably at lower temperatures. In some or all embodiments of the present invention, one or more promoters are selected from the list consisting of ruthenium, palladium, platinum, rhodium, rhenium, manganese, chromium, nickel, iron, molybdenum, tungsten, zirconium, gallium, thorium, lanthanum, cerium and mixtures thereof. Preferably the promoter is manganese. When a promoter is present, the one or more promoters are typically used in a total amount from 0.1 wt. % to 3 wt. %, on elemental basis, based on the total weight of the supported synthesis catalyst.

The addition of the promoters, dispersion aids, strength aids, or binders may be integrated at several stages of the process according to the present invention. Preferably, the promoter, dispersion aids, strength aids and/or binders are introduced during the impregnation step.

The process of the present invention allows for the preparation of a supported Fischer-Tropsch synthesis catalyst having a high cobalt loading, for example, at least 15 wt. %. Consequently, a reduced synthesis catalyst obtained by means of the process of the present invention may have commensurately higher activity in Fischer-Tropsch reactions.

The present invention therefore also provides a cobalt-containing Fischer-Tropsch catalyst obtained or obtainable by the process of the present invention.

The Fischer-Tropsch synthesis catalyst prepared in accordance with the present invention may conveniently be converted into a reduced Fischer-Tropsch synthesis catalyst by reductive activation by any known means of which the skilled person is aware which is capable of converting cobalt oxide to the active cobalt metal. Thus, in one embodiment, the process of the invention further comprises reducing the cobalt-containing Fischer-Tropsch synthesis catalyst obtained to form a reduced Fischer-Tropsch synthesis catalyst.

The step of forming a reduced Fischer-Tropsch synthesis catalyst may be carried out batch wise or continuously in a fixed bed, fluidised bed or slurry phase reactor. The reduced synthesis catalyst formed following the reductive activation process is useful in the heterogeneously catalysed production of hydrocarbons from syngas by Fischer-Tropsch synthesis, for example in the production of a diesel or aviation fuel or precursor thereof. Fischer-Tropsch synthesis of hydrocarbons from syngas may be represented by Equation 1:

$$mCO + (2m+1)H_2 \rightarrow mH_2O + C_mH_{2m+2} \qquad \text{Equation 1}$$

As discussed hereinbefore, the process of the present invention has been surprisingly found to afford a Fischer-Tropsch catalyst exhibiting high $C_{5+}$ hydrocarbon selectivity. Furthermore, at least in some embodiments, the catalytic activity has also been found to be superior.

In another aspect, a method for increasing the selectivity of a Fischer-Tropsch process for the production of $C_{5+}$ hydrocarbons and/or increasing conversion in a Fischer-Tropsch process is provided, said method comprising the step of supplying a cobalt-containing Fischer-Tropsch synthesis catalyst as defined hereinabove to a Frischer-Tropsch process.

The present invention also provides a use of a cobalt-containing or Fischer-Tropsch synthesis catalyst as defined hereinbefore for the production of $C_{5+}$ hydrocarbons and/or increasing conversion in a Fischer-Tropsch process.

In a further aspect, the present invention provides a process for converting a feed comprising a mixture of hydrogen and carbon monoxide gases, preferably in the form of a synthesis gas mixture, to hydrocarbons, which process comprises contacting a mixture of hydrogen and carbon monoxide, preferably in the form of a synthesis gas mixture, with a cobalt-containing Fischer-Tropsch catalyst as defined hereinbefore.

In the Fischer-Tropsch reaction described above, the volume ratio of hydrogen to carbon monoxide ($H_2$:CO) in the gaseous reactant mixture is preferably in the range of from 0.5:1 to 5:1, more preferably from 1:1 to 3:1, for example in the range of from 1.6:1 to 2.2:1. The gaseous reactant stream may also comprise other gaseous components, such as nitrogen, carbon dioxide, water, methane and other saturated and/or unsaturated light hydrocarbons, each preferably being present at a concentration of less than 30% by volume. The temperature of the Fischer-Tropsch reaction is preferably in the range from 100 to 400° C., more preferably from 150 to 350° C., and most preferably from 150 to 250° C. The pressure is preferably in the range from 1 to 100 bar (from 0.1 to 10 MPa), more preferably from 5 to 75 bar (from 0.5 to 7.5 MPa), and most preferably from 10 to 50 bar (from 1.0 to 5.0 MPa).

The cobalt hydroxide nitrate may be prepared by any suitable method familiar to the skilled person. For example, cobalt hydroxide nitrate may be prepared by controlled hydrolysis of $Co(NO_3)_2$ in sodium hydroxide solution, as described in L Markov et al., Thermochim Acta, 1986, 106, pages 283 to 292. Alternatively, cobalt hydroxide nitrate may be prepared by using $NaHCO_3$ and urea as the hydrolysis reagents as described in K. Petrov et al., Journal of Solid State Chemistry, 1992, 101, pages 145 to 153. Nevertheless, the present invention also provides a further process for the preparation of cobalt hydroxide nitrate, as described below.

Thus, in another aspect, the present invention provides a process for preparing cobalt hydroxide nitrate, or a hydrate thereof, as described above. This process for preparing cobalt hydroxide nitrate, or a hydrate thereof, comprises the step of reacting cobalt hydroxide with cobalt nitrate. The reaction is suitably performed in solution, preferably aqueous solution (e.g. in deionized water) and at above room temperature.

Preferably, the reaction is conducted at a temperature of from 40° C. to 80° C., more preferably from 50° C. to 70° C., most preferably 55° C. to 65° C.

In some embodiments, cobalt hydroxide and cobalt nitrate are contacted in solution with agitation (e.g. vigorous stirring) for a suitably length of time in order for the reaction to progress. For example, cobalt hydroxide and cobalt nitrate may be contacted in solution for at least 10 minutes, for example from 10 minutes to 2 hours, such as from 30 to 90 minutes, for example from 50 to 75 minutes. Progress of the reaction may be conveniently monitored by observing a colour change from scarlet red to purple.

Preferably the molar ratio of cobalt nitrate to cobalt hydroxide in the preparation of cobalt hydroxide nitrate is from 1:1 to 5:1, more preferably in the range 2:1 to 4:1. In some instances, cobalt nitrate may be in the form of cobalt nitrate hexahydrate.

In some embodiments, cobalt hydroxide and cobalt nitrate are reacted in the presence of nitric acid. Preferably the molar ratio of cobalt hydroxide to nitric acid in the preparation in these embodiments is 1:1 to 5:1, more preferably from 2:1 to 5:1.

In yet a further aspect, the present invention also provides a use of cobalt hydroxide nitrate for increasing the elemental cobalt metal loading on a supported cobalt-containing Fischer-Tropsch synthesis catalyst which is obtainable in a single impregnation step.

The invention will now be further described by reference to the following examples which are illustrative only. In the examples, CO conversion is defined as moles of CO used/moles of CO fed×100, and carbon selectivity as moles of CO attributed to a particular product/moles of CO converted× 100. Unless otherwise stated, temperatures referred to in the examples are applied temperatures and not catalyst/bed temperatures. Unless otherwise stated, pressures referred to in the examples are absolute pressures.

The present invention will now be illustrated by way of the following examples and with reference to the following FIGURE:

FIG. 1: PXRD pattern (top) and phase identification results (bottom) of an extrudate prepared by the process of the invention.

EXAMPLES

Example 1—Preparation of Cobalt Hydroxide Nitrate from Cobalt Hydroxide and Cobalt Nitrate A predetermined amount of deionized water was weighed, the desired amount of cobalt nitrate hexahydrate $(Co(NO_3)_2.6H_2O)$ was added and the solids dissolved under vigorous stirring at 60° C. Cobalt hydroxide $(Co(OH)_2)$ was added to the solution in an amount so as to achieve a molar ratio of $Co(OH)_2:Co(NO_3)_2.6H_2O$ of 1:3. The solution was maintained at a temperature of 60° C. with agitation for 60 min, upon which the colour of the solution changed from scarlet red to purple.

Example 2—Preparation of Cobalt Hydroxide Nitrate from Cobalt Hydroxide, Cobalt Nitrate, and Nitric Acid A predetermined amount of deionized water was weighed and the desired amount of nitric acid was added in a glass reactor associated with a heater and adjustable agitation system. Cobalt hydroxide $(Co(OH)_2)$ was added to the solution in an amount so as to achieve a molar ratio of $HNO_3:Co(OH)_2$ of 1:2 and the solids dissolved under vigorous agitation. Cobalt nitrate hexahydrate $(Co(NO_3)_2.6H_2O)$ was then added to the solution so as to achieve a molar ratio of $Co(NO_3)_2.6H_2O:Co(OH)_2$ of 1:1. The resulting solution was heated to 60° C. and maintained at 60° C. with agitation for 60 min, upon which the colour of the solution changed from scarlet red to purple.

Example 3—Preparation of Catalyst Extrudates

An appropriate quantity of titania powder (Evonik Aeroxide P25) was weighed so as to achieve a weight ratio of elemental cobalt (Co) present in the solution prepared in either Example 1 or 2 to titania to achieve a weight percentage of cobalt in the final extrudate of 20 wt. %. The solution prepared in either Example 1 or 2 was slowly added to the titania with stirring so as to reduce the volume of the powder. The mixture was then transferred to a mechanical mixer (Vinci mixer or Simpson Muller) and kneaded into extrudable paste. The wetness of the paste was adjusted with water as needed so as to form an extrudable paste. The mixture was then extruded into green extrudates with the desired geometry. The extrudates were dried and calcined using the following profile: 60° C. for 5 h, 120° C. for 5 h, 300° C. for 2 h; ramp rate in between is 2.0° C./min.

FIG. 1 shows the PXRD pattern of the extrudates dried at 120° C. The lines attributed to cobalt hydroxide nitrate hydrate are clearly discernible, as are various titanium oxides (anatase and rutile) and cobalt nitrate hydrate. The cobalt hydroxide $(Co(OH)_2)$ used in the synthesis is not observed, suggesting the complete conversion of this compound.

Example 4—Use of Catalyst Extrudates in a Fischer-Tropsch Synthesis Process

The cobalt species in the catalyst extrudates were fully reduced to cobalt metal using hydrogen before the reaction. The products in gas phase were analysed using an on-line GC equipped with a FID. The liquid products were collected in cryogenic containers and analysed off line. The operation conditions and results of the reaction are listed as follows:

Space velocity: 1250 $h^{-1}$
Reaction pressure: 42 barg
$H_2/CO$ molar ratio: 1.8
Time on stream: 600 h
Average reaction temperature: 192° C.
Average conversion of CO: 64.29%
Average selectivity of CO to $C_{5+}$ hydrocarbons: 86.76%
Average selectivity of CO to methane: 7.02%

Comparative Example 1—Preparation of Catalyst Extrudates Using Conventional Cobalt nitrate hexahydrate as the cobalt source A predetermined amount of cobalt nitrate hexahydrate $(Co(NO_3)_2.6H_2O)$ was weighed and dissolved in a minimum amount water to form a clear solution at room temperature. To this solution was added a predetermined amount of titania powder (Evonik Aeroxide P25). The mixture was then transferred to a mechanical mixer (Vinci mixer or Simpson Muller) and kneaded into a paste. The wetness of the paste was adjusted with water as needed so as to form an extrudable paste. The mixture was then extruded into green extrudates with the desired geometry. The extrudates were dried and calcined using the following profile: 60° C. for 5 h, 120° C. for 5 h, 300° C. for 2 h; ramp rate in between is 2.0° C./min. The resultant catalyst had 10 wt. % of Co metal, which represents the maximum Co loading achieved by conventional methods.

Comparative Example 2—Use of Conventional Catalyst Extrudates in a Fischer-Tropsch Synthesis Process The cobalt species in the catalyst extrudates were fully reduced to cobalt metal using hydrogen before the reaction. The products in gas phase were analysed using an on-line GC equipped with a FID. The liquid products were collected in cryogenic containers and analysed off-line. The operation conditions and results of the reaction are listed as follows:
Space velocity: 1250 h$^{-1}$
Reaction pressure: 42 barg
H$_2$/CO molar ratio: 1.8
Time on stream: 600 h
Average reaction temperature: 199.5° C.
Average conversion of CO: 63.52%
Average selectivity of CO to C$_{5+}$ hydrocarbons: 84.13%
Average selectivity of CO to methane: 8.33%
A Fischer-Tropsch catalyst was not prepared using Co(OH)$_2$ because of its poor solubility in water.

The above results demonstrate the usefulness of the catalyst according to the present invention in the Fischer-Tropsch process. Comparing the performance data of the catalyst with 10 wt % Co loading formed using conventional methods (Comparative Example 2) and the catalyst with 20 wt. % Co loading prepared according to the present invention (Example 4), it is clear that the catalyst prepared in the current invention is superior. Example 4 shows an average CO conversion of 64.29% at 192° C., whereas the catalyst made in Comparative Example 2 only reaches a CO conversion of 63.52% at 199.5° C. The decreased reaction temperature required in Example 4 when compared to Comparative Example 2 results in lower methane selectivity (7.02% vs. 8.33%) and higher C$_{5+}$ hydrocarbon selectivity (86.76% vs. 84.13%), which is highly desirable in a Fischer-Tropsch process.

The invention claimed is:

1. A process for preparing a titania supported cobalt-containing Fischer-Tropsch synthesis catalyst, said process comprising the steps of:
    (a) impregnating a titania support material with cobalt hydroxide nitrate, or a hydrate thereof, of formula (I) below to form an impregnated support material, $$[Co(OH)_x(NO_3)_{(2-x)}.yH_2O] \quad (I)$$

where: 0<x<2
    0≤y≤6
    (b) drying and calcining the impregnated support material.

2. A process for preparing a supported cobalt containing Fischer-Tropsch synthesis catalyst, said process comprising the steps of:
    (i) impregnating a support material with cobalt hydroxide nitrate, or a hydrate thereof, of formula (I) below to form an impregnated support material, $$[Co(OH)_x(NO_3)_{(2-x)}.yH_2O] \quad (I)$$

where: 0<x<2, and
    0≤y≤6;
    (ii) forming shaped particles from the impregnated support material; and
    (iii) drying and calcining the shaped particles.

3. A process according to claim 1, wherein x is at most 1.5.

4. A process according to claim 2, wherein in step (ii), the shaped particles are formed by extrusion.

5. A process according to claim 1, wherein the support material is in the form of a powder or granulate and impregnation step (a) forms an impregnated support powder or granulate and calcination in step (b) forms a calcined powder or granulate, the process further comprising extruding the calcined powder or granulate to form an extrudate.

6. A process according to claim 5, wherein the support material is in the form of a powder having a median particle size diameter (d50) of less than 50 μm; or wherein the support material is in the form of a granulate having a median particle size diameter (d50) of from 300 to 600 μm.

7. A process according claim 1, wherein the average pore radius of the support material prior to impregnation is in the range of from 10 to 500 Å.

8. A process according to claim 1, wherein the support material is in the form of an extrudate and impregnation step (a) forms an impregnated extrudate prior to step (b).

9. A process according to claim 1, wherein the support material has not previously been impregnated with a cobalt-containing compound and the impregnation step of the process is the only step in which cobalt-containing compound is introduced to the support material prior to calcination.

10. A process according to claim 1, wherein impregnation step affords a synthesis catalyst containing greater than or equal to 10 wt. % of cobalt, on an elemental basis, based on the total weight of the supported synthesis catalyst.

11. A process according to claim 1, wherein the support material is impregnated with an aqueous solution or suspension of cobalt hydroxide nitrate.

12. A process according to claim 1, wherein the support material comprises a material selected from any of silica, alumina, silica-alumina, ceria, gallia, zirconia, titania, magnesia, zinc oxide, and mixtures thereof.

13. A process according to claim 12, wherein the support material is a titania and selected from titanium dioxide anatase, titanium dioxide rutile, titanium dioxide brookite and combinations thereof.

14. A process according to claim 1, wherein the cobalt-containing Fischer-Tropsch synthesis catalyst obtained comprises one or more promoters, dispersion aids, strength aids and/or binders, optionally further comprising wherein the one or more promoters, dispersion aids, strength aids and/or binders, or precursors thereof, is/are introduced during impregnation step.

15. A process according to claim 14, wherein the cobalt-containing Fischer-Tropsch synthesis catalyst obtained comprises one or more promoters selected from the group consisting of ruthenium, palladium, platinum, rhodium, rhenium, manganese, chromium, nickel, iron, molybdenum, tungsten, zirconium, gallium, thorium, lanthanum, cerium and mixtures thereof.

16. A process according to claim 15, wherein the one or more promoters are present in the cobalt-containing Fischer- Tropsch synthesis catalyst obtained in an amount from 0.1 wt. % to 3 wt. %, on an elemental basis, based on the total weight of the supported synthesis catalyst.

17. A process according to claim 1, wherein the calcining is conducted at a temperature of at least 250° C.

18. A process according to claim 1, further comprising reducing the cobalt-containing Fischer-Tropsch synthesis catalyst obtained to form a reduced Fischer-Tropsch synthesis catalyst.

19. A process for preparing cobalt hydroxide nitrate, or a hydrate thereof, of formula (I):

$$[Co(OH)_x(NO_3)_{(2-x)}.yH_2O] \quad (I)$$

where: $0 < x < 2$, and
$0 \leq y \leq 6$;

said process comprising the step of reacting cobalt hydroxide with cobalt nitrate.

20. A process according to claim 19, wherein cobalt nitrate is in the form of cobalt nitrate hexahydrate.

21. A process according to claim 19, wherein cobalt hydroxide is reacted with cobalt nitrate in solution.

22. A process according to claim 19, wherein cobalt hydroxide and cobalt nitrate are reacted in the presence of nitric acid.

23. A process according to claim 19, wherein the molar ratio of cobalt nitrate to cobalt hydroxide is from 1:1 to 5:1.

24. The process according to claim 1, wherein no $Co(OH)_2$ is observed after drying as measured by powder x-ray diffraction.

25. The process according to claim 1, wherein the cobalt hydroxide nitrate, or a hydrate thereof, is prepared by reacting cobalt hydroxide with cobalt nitrate.

26. The process according to claim 25, wherein the reacting is performed for at least 10 minutes prior to impregnation.

27. The process according to claim 1, wherein the impregnating of the titania support material with cobalt hydroxide nitrate or hydrate thereof comprises providing a purple solution of cobalt hydroxide nitrate or a hydrate thereof; then contacting the purple solution with the titania support to impregnate it.

28. The process according to claim 1, wherein the providing the purple solution of cobalt hydroxide nitrate or the hydrate thereof comprises reacting cobalt hydroxide with cobalt nitrate in aqueous solution for at least ten minutes, before the contacting of the purple solution with the titania support.

* * * * *